United States Patent [19]
Renauld et al.

[11] Patent Number: 5,935,929
[45] Date of Patent: Aug. 10, 1999

[54] METHODS FOR TREATING INTERSTITIAL LUNG DISEASE BY USING INTERLEUKIN-9 AND ITS ANTAGONISTS

[75] Inventors: Jean-Christophe Renauld; Mary-Christine Many; Francois Huaux; Dominique Lison, all of Brussels, Belgium

[73] Assignee: Ludwig Institute for Cancer Research, New York, N.Y.

[21] Appl. No.: 08/925,348

[22] Filed: Sep. 8, 1997

Related U.S. Application Data

[63] Continuation-in-part of application No. 08/706,302, Aug. 30, 1996, Pat. No. 5,830,454.

[51] Int. Cl.$^6$ .................................................. A61K 38/00
[52] U.S. Cl. .............................. 514/12; 514/2; 514/885; 514/860; 514/813; 424/85.1; 424/85.2
[58] Field of Search .................................... 424/85.1, 85.2, 424/55.7; 514/2, 12, 885, 860, 813

[56] References Cited

U.S. PATENT DOCUMENTS

| | | | |
|---|---|---|---|
| 5,132,109 | 7/1992 | Dugas et al. | 424/85.2 |
| 5,414,071 | 5/1995 | Yang et al. | 530/351 |
| 5,830,454 | 11/1998 | Renauld | 530/351 |

OTHER PUBLICATIONS

Immunology, ed. Roitt et al., pp. 13.19 and 23.1–23.11, 1985.

Biomed & Pharmacother, SM Hsu, 48, 433–444, 1944.

American Journal of Pathology, Rakesh K. Kumar, vol. 135, No. 4, 1989.

Thorax, Naohito Suzuki et al., vol. 51, 1036–1042, 1996.

Many, et al., "Two-step developoment of Hashimoto–like thyroiditis in genetically autoimmune prone non–obese diabetic mice: effects of iodine–induced cell necrosis", J. Endocrinol 147: 311–320 (1995).

Remick et al., ed., "Cytokines in Health and Disease", 2nd ed., Marcel Dekker, Inc. (New York, 1997), pp. 133–141, 519–529.

Kurzrock et al., "Cytokines: Interleukins and Their Receptors", Kluwer Academic Publishers, Boston, 1995, pp. 143–157, 187–303, discuss IL–4 (pp. 143–157, and IL–9 (287–303).

Brennan et al., ed., "Cytokines in Autoimmunity", Chapman & Hall, Austin, 1996, pp. 1–5, 9–20, 25–31, 49–53, 65–75, 77–81, 101–119, 121, 137–139, and 153–157.

*Primary Examiner*—F. T. Moezie
*Attorney, Agent, or Firm*—Fulbright & Jaworski, LLP.

[57] ABSTRACT

A method for the treatment and prevention of immune disorders and fibrosis associated disorders is disclosed. The method involves administering interleukin-9 in an effective amount to the subject. Among the conditions treatable are thyroiditis, autoimmune diabetes and silicosis.

6 Claims, 10 Drawing Sheets

METHODS FOR TREATING INTERSTITIAL LUNG DISEASE BY USING INTERLEUKIN-9 AND ITS ANTAGONISTS

RELATED APPLICATION

This is a continuation-in-part of Ser. No. 08/706,302, filed Aug. 30, 1996, now U.S. Pat. No. 5,830,454 and incorporated by-reference herein.

FIELD OF THE INVENTION

This invention relates to the treatment of pathological conditions which are treatable via administration of interleukin-9 ("IL-9") or interleukin-9 analogs, antagonists, and so forth. In particular, fibrotic, and autoimmune diseases are treatable via administration of IL-9 or its analogs, alone or together with other drugs.

BACKGROUND AND PRIOR ART

Interleukin-9 ("IL-9" hereafter), is a glycoprotein which has been isolated from both murine and human cells. See, e.g., U.S. Pat. No. 5,208,218, incorporated by reference. This reference also teaches isolated nucleic acid molecules encoding the protein portion of the molecule, and how to express it.

Various uses of the molecule can be seen in, e.g., U.S. Pat. No. 5,164,317 (proliferation of mast cells); U.S. Pat. Nos. 5,246,701 and 5,132,109 (enhancing production of IgG and inhibiting production of IgE), in addition to its first recognized utility, which is as a T cell growth factor. Exemplary of the vast scientific literature on the molecule are Van Snick, et al, *J. Exp. Med.* 169(1): 363–368 (1989) (cDNA for the murine molecule, then referred to as P40). Houssiau, et al, J. Immunol 148(10): 3147–3151 (1992) (IL-2 dependence of IL-9 expression in T lymphocytes). Renauld, et al, Oncogene 9 (5): 1327–1332 (1994) (effect on thymic lymphomas); Renauld, et al, Blood 85(5): 1300–1305 (1995) (anti-apoptotic factor for thymic lymphoma). Review articles may be found at, e.g., Renauld, et al, Cancer Invest 11(5): 635–640 (1993); Renauld, et al, Adv. Immunol 54: 79–97 (1993).

There is no literature on the influence of IL-9 on autoimmune disorders.

The art is familiar with a vast number of autoimmune disorders, which are classified in various ways. One way of classification is by way of the aspect of the immune system most intimately involved with the disorder. For example, in humoral response associated autoimmune diseases, B cells are involved. Antibodies are generated against self molecules, such as the acetylcholine receptor (myasthenia gravis), or the TSH receptor (Graves disease). In autoimmune diseases involving a cellular response, T cells, macrophages, and NK cells react with self molecules. Exemplary of these conditions are insulin dependent diabetes and thyroiditis. This family of diseases result, inter alia, from a skewing of Th1/Th2 balance.

One problem in the study of autoimmune diseases is the absence of suitable animal models. Without an appropriate system for studying a particular condition, one cannot draw conclusions as to the potential efficacy of a given drug in a therapeutic context.

An appropriate animal model for cell mediated diseases does exist, however, and it has been used in the disclosure which follows. Using the specific case of induced thyroiditis in a murine model, it has now been shown that IL-9 has therapeutic efficacy in Th1 associated autoimmune disorders. This will be shown in the detailed description of preferred embodiments which follows.

The murine model used in the disclosure which follows is also one which can be used to study diseases such as sialoadenitis, autoimmune hemolytic anemia, and other conditions. Further, a murine model is available which is useful in studying pathologies involving fibrosis, such as interstitial lung disease. Characteristic of these fibrosis related pathologies is inflammation in the afflicted tissue or organ, leading to scarring and distortion of tissue. Exemplary of this group of pathologies are interstitial lung diseases such as silicosis, asbestosis, white lung disease, black lung disease, Shaver's disease, etc. These conditions are known as pneumoconioses, (or anthracotic tuberculosis), and involve inflammation and lung fibrosis, caused, e.g., by inhalation of fine mineral particles. Other fibrotic conditions include all forms of sclerosis, fibrosis related rheumatism, such as chronic rheumatoid arthritis, and collagen related fibrosis, such as conditions involving keloids, scarring, renal diseases involving related conditions, and so forth.

The murine models for these conditions have been employed, as will be seen infra, to show the efficacy of IL-9 in their treatment.

BRIEF DESCRIPTION OF THE FIGURES

FIG. 4A shows immunostaining without IL-9 and 4B with it.

DETAILED DESCRIPTION OF PREFERRED EMBODIMENTS

EXAMPLE 1

Figure 1A:
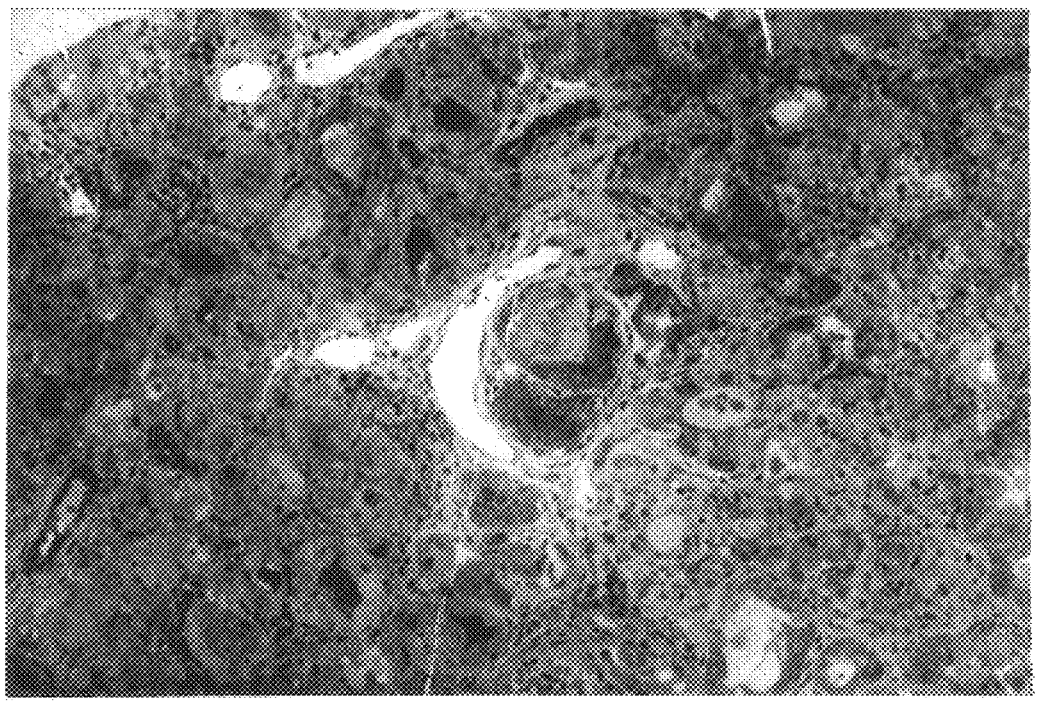
FIG. 1A shows effect of high doses of iodide following induction of goiter in NOD mice.

Two strains of mice, i.e., the FVB strain, and the NOD strain, were used in the experiments which follow. The NOD strain of mice is recognized as an appropriate model for studies on human diseases. This is because the strain is a non-obese, diabetic mouse (hence "NOD"), which spontaneously develops pancreatic and thyroid lesions resulting from autoimmune disorders, such as diabetes. The mouse strain is also useful as a model for pathogenesis and immunotherapy of autoimmune disease, such as cell mediated autoimmune diseases. See, e.g., Many, et al, J. Endrocrinol 147: 311–320 (1995); Male, et al, Advanced Immunology Third Edition (1996). pg. 12.15; Kikutani, et al, Adv. Immunol 51: 285–322 (1992) all of which are incorporated by reference. Specifically, with reference to autoimmune diabetes, mononuclear cell infiltration of pancreatic islets is detected as soon as 4–6 weeks of age, followed by destruction of insulin producing pancreatic islet β cells.

Th1 cells are associated in this process of inflammation of islets of Langerhans. This, in turn leads to diabetes in 70%–80% of females, and 20% of males, after 30 weeks. This is borne out by studies which show acceleration of onset following administration of IL-12, and protection with IL-4 or IL-10. See, e.g., Trembleau et al., J. Exp. Med. 181: 817–821 (1995); Rapaport et all, J. Exp. Med. 178: 87–89 (1993); Rabinovitch et al., Transplantation 60: 368–374 (1995). Many, et al, supra, suggest that the same mechanism is involved in thyroiditis. Hence, the NOD strain is an appropriate model for the work which follows.

Two month old female NOD mice (haplotype H-2g) were used, as were two month old female FVB mice (haplotype H-2q), as a control. The FVB mice can be treated with iodine to develop transient thyroiditis, while the NOD mice develop a persistent form of the condition. Also, the intensity of CD4$^+$ T cell infiltration in affected organs differs. See infra.

Mice were made goitrous by feeding them a low iodine diet (0.1 ug iodine per day), supplemented with 0.25% propylthiouracil for 10 days, followed by the low iodine diet alone, for another 2 days. They then received high doses of iodine (10 ug/day), via intraperitoneal injection, for 4 days. Five mice from each strain also received 1 ug/day of recombinant, murine interleukin-9, for 6 days. The interleukin-9 was administered in 0.2 ml/volumes of PBS via intraperitoneal injection, starting 2 days before the high iodine diet was administered. In controls, only PBS was administered. Interleukin-4 ("IL-4") was used as a control with the NOD mice.

Following treatment, mice were anaesthetized with an intraperitoneal injection of 7.5 mg of Nembutal, diluted with saline solution 1/3. Blood samples were collected to measure thyroxin levels via a radio-immunoassay, and then the thyroid glands were removed. One lobe of each gland was designated for morphological and stereological analysis, and the other for immunohistochemical analysis.

To carry out the former, lobes were immersed for 2 hours in 2.5% glutaraldehyde in 0.1M cacodylate buffer, post fixed for 1 hour in 1% osmium tetroxide, and embedded in resin. Sections were cut to 0.5 um thickness, and were stained with toluidine blue. Relative volumes of the various glandular components were measured with a projection microscope.

Immunohistochemical analysis was carried out by quick freezing lobes in isopentane cooled in liquid nitrogen. Cryostat sections were taken, and used for immuno peroxidase staining, following Toussaint-Demylle, et al Autoimmunity 7:51–62 (1990), using a monoclonal antibody specific for CD4$^+$ T cells, and one specific for B cells.

Numbers of the cell types (CD4+, B+) were evaluated via magnification (×250), in ten microscopic fields chosen at random from thyroid sections.

The results from these experiments are presented in FIGS. 1–5 and Tables 1 and 2, which are discussed infra.

These show that administration of a high dose of iodide after goitrogenic treatment had a strong necrotic effect on thyroid cells. Cell debris accumulated in the follicular lumina. After 4 days of treatment, cell necrosis was associated to the interstitial infiltration of inflammatory cells.

After the 6 days of IL-9 administration which started two days before the high iodide diet began, the histology of the thyroid of the FVB mice was very similar to what was obtained with a high iodide diet alone. Signs of cell necrosis and of thyroiditis were evident, and analysis suggested that the IL-9 aggravated the interstitial infiltration of inflammatory cells. The relative volume of the interstitium was higher than in those control mice (FVB mice), which were not treated with IL-9. See Table 2.

Figure 1B:
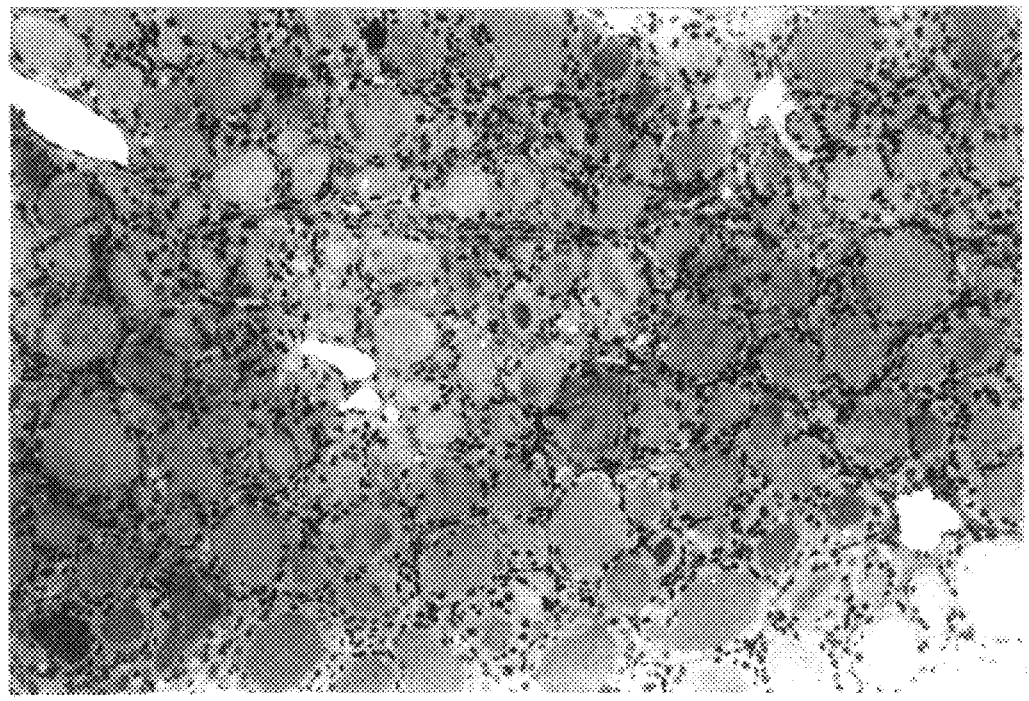
FIG. 1B shows the effect of IL-9 on iodide treated NOD mice.
Figure 1C:
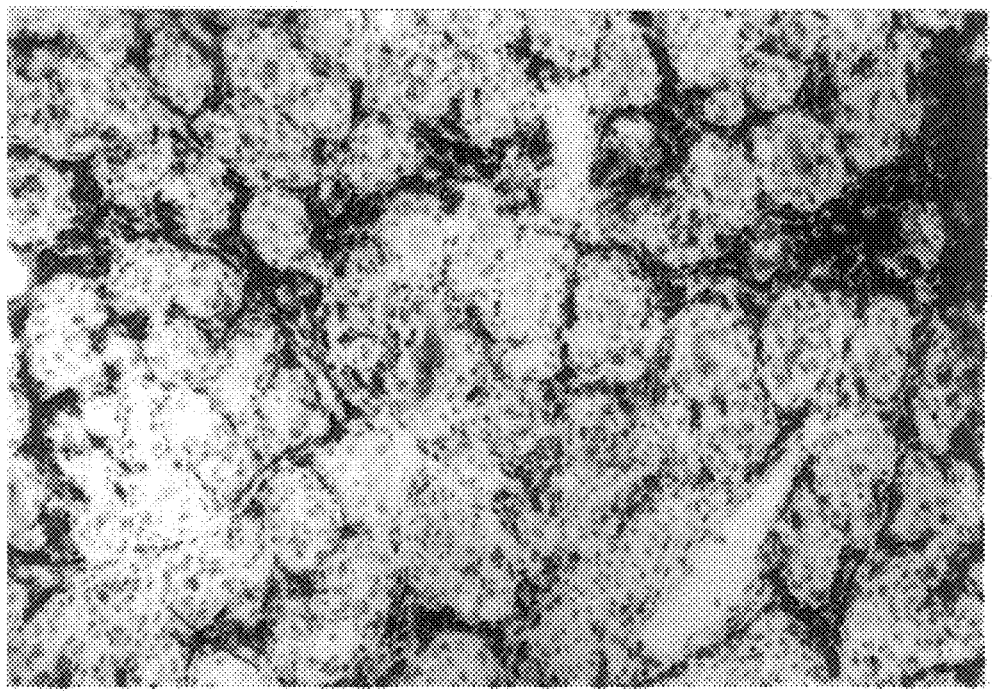
FIG. 1C shows staining for $CD4^+$ T cells in thyroids of goitrous NOD mice after a high iodide diet and without IL-9.
Figure 1D:
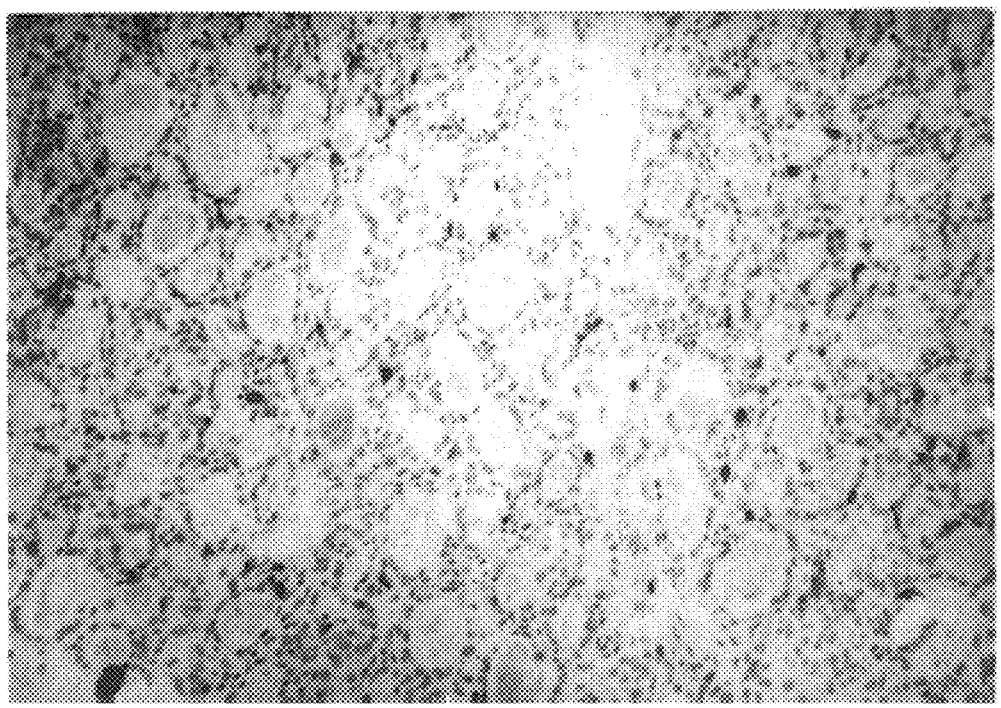
FIG. 1D is comparable to 1C, but shows results with IL-9.

In FIG. 1A, it can be seen that in the case of the goitrous NOD mice, all the follicular lumina were filled with necrotic debris, and the interstitium was extensively infiltrated by inflammatory cells. In contrast to the FVB mice, administration of IL-9 to the goitrous NOD mice prevented thyroid-induced thyroiditis. FIG. 1B shows that the large follicular lumina contained little necrotic debris, and few inflammatory cells were found in the interstitium. Table 1 shows that its relative volume was significantly decreased after IL-9 treatment. The relative volumes of epithelium and colloid were increased, as compared to mice which had not received the IL-9. A significant drop in thyroid weight was also observed after administration of the IL-9.

With respect to immunohistochemical analysis, the cells which infiltrated the thyroids of goitrous FVB mice treated with the iodide for 4 days were mainly MHC-Class II positive APCs, as well as T cells. CD4$^+$ T helper cells predominated in this group. The administration of IL-9 increased the number of CD4$^+$ cells, but increased the number of B cells even more so. The data for NOD mice are set forth in Table 1, and those for FVB mice in Table 2, which follows, infra.

In contrast, administration of iodide to NOD mice resulted in infiltration of numerous CD4$^+$ T cells, and few B cells. When IL-9 was administered, the number of infiltrating CD4$^+$ cells was drastically reduced. See FIGS. 1C and 1D.

TABLE 1

| Treatment | Thyroid weight | Relative volumes | | | Infiltrate | |
| | | Epithelium | Colloid | Interstitium | CD4+ T cells | B220+ B Cells |
| --- | --- | --- | --- | --- | --- | --- |
| NO | 3.0 ± 0.3 | 38.2 ± 2.7 | 46 ± 2.7 | 14.0 ± 2.0 | 2.2 ± 0.5 | 0.5 ± 0.1 |
| GOITER (G) | 6.9 ± 0.1* | 73.5 ± 0.6* | 6.5 ± 0.6* | 20.0 ± 0.5* | 5.6 ± 0.5* | 0.6 ± 0.1 |
| G + HID | 7.3 ± 0.4* | 45.9 ± 2.9* | 15.4 ± 5.1* | 38.7 ± 5.7* | 46.6 ± 5.3* | 1.9 ± 0.6* |
| G + HID + IL-9: 6 days | 4.5 ± 0.7°* | 54.1 ± 3.6°* | 32.0 ± 3.1°* | 13.8 ± 1.9° | 2.9 ± 0.3° | 1.3 ± 0.1* |
| G + HID + IL-9: 4 days | 4.6 ± 0.4°* | n.d | n.d | n.d | 3.1 ± 0.4°* | 1.6 ± 0.1* |
| G + HID + IL-9: 1 inj. | 4.9 ± 0.3°* | n.d | n.d | n.d | 4.6 ± 0.5°* | 1.5 ± 0.16* |
| G + HID + IL-4: 6 days | 6.4 ± 0.7* | n.d | n.d | n.d | 42.3 ± 4.8* | 7.1 ± 3.8°* |

*Mean (± SD, n = 5) thyroid weight (mg), relative volumes (%) of the various glandular components, and numbers of CD4+ and B220+ cells per ten follicular profiles, in thyroids of untreated and goitrous NOD mice and of goitrous NOD mice treated for 4 days with iodide (HID) alone, iodide plus IL-9, or iodide plus IL-4.
°$p < 0.05$ vs HID treated mice
*$p < 0.05$ vs untreated mice

TABLE 2

| Treatment | Thyroid weight | Relative volumes | | | Infiltrate | |
| | | Epithelium | Colloid | Interstitium | CD4+ T cells | B220+ B Cells |
| --- | --- | --- | --- | --- | --- | --- |
| G + HID | 5.8 ± 0.4 | 55.8 ± 5.5 | 17.2 ± 2.4 | 27.0 ± 3.7 | 3.53 ± 0.8 | 2.05 ± 0.2 |
| G + HID + IL-9: 6 days | 5.9 ± 0.5 | 46.8 ± 3.9° | 18.8 ± 1.1 | 34.4 ± 4.1° | 7.97 ± 1.3° | 10.3 ± 0.8° |

*Mean (± SD, n = 5) thyroid weight (mg), relative volumes (%) of the various glandular components, and numbers of CD4+ and B220+ cells per ten follicular profiles, in thyroids of goitrous FVB mice treated for 4 days with iodide (HID) alone or plus IL-9.
°$p < 0.05$ vs HID treated mice These results suggested additional experiments to determine the minimal length of treatment which would produce the desired effect, specifically, parallel experiments were carried out where the original six daily treatments were reduced to four, or one single injection. Similar results were secured, indicating that only a very short treatment is needed. See Table 1, supra.

Figure 1E:
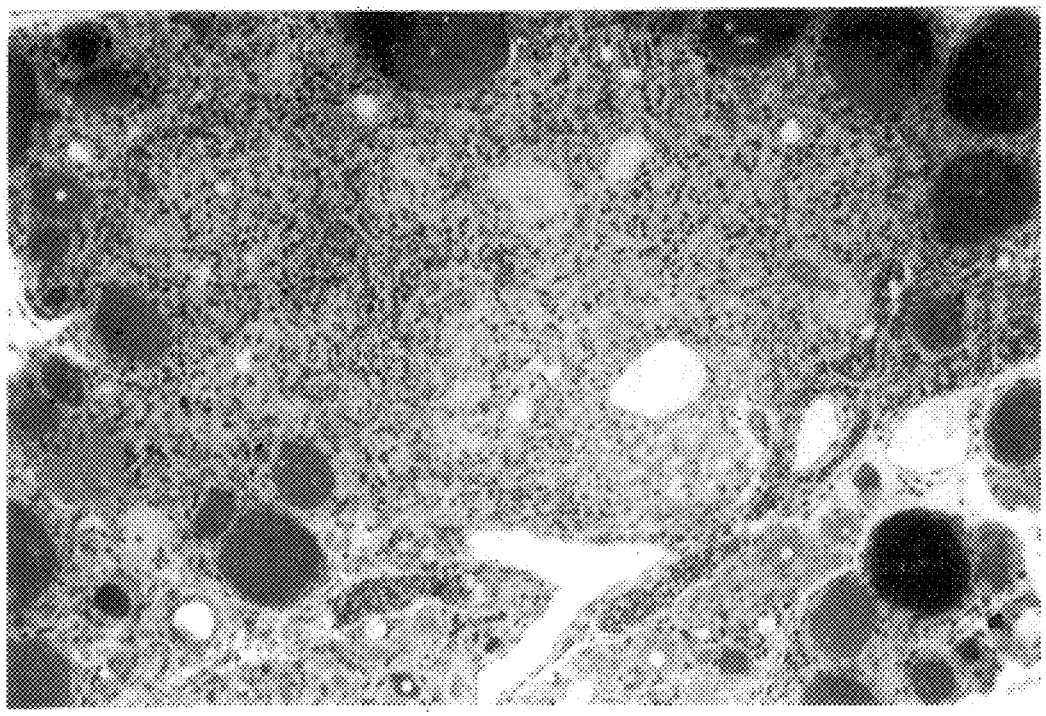
FIGS. 1E and 1F show the result of experiments testing long term IL-9 therapy.
Figure 1F:
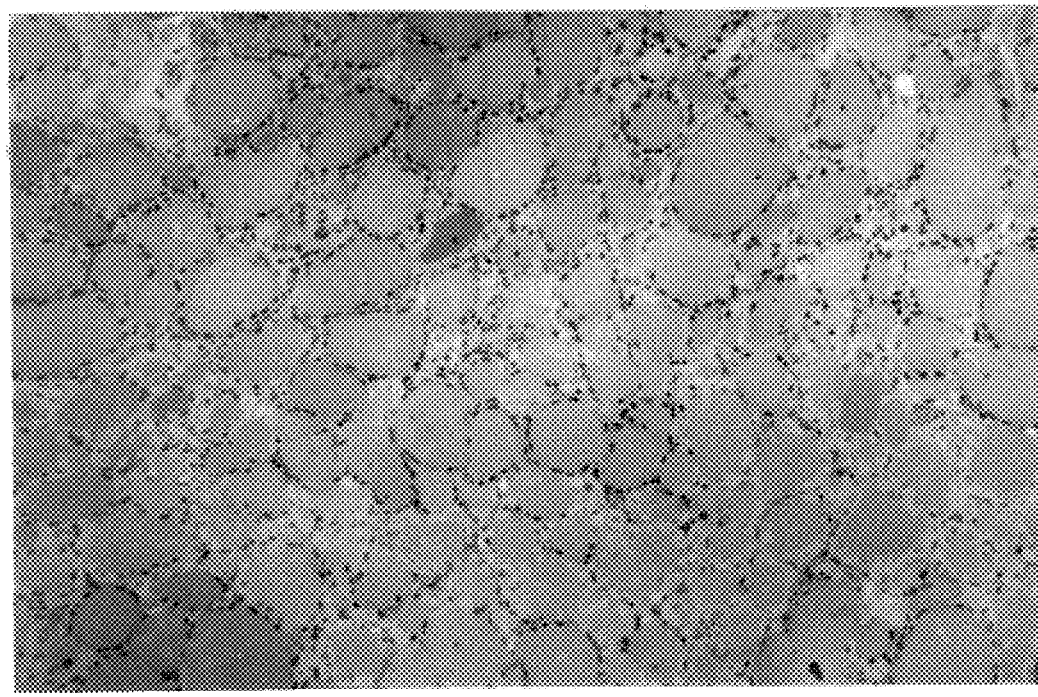
Figure 1G:
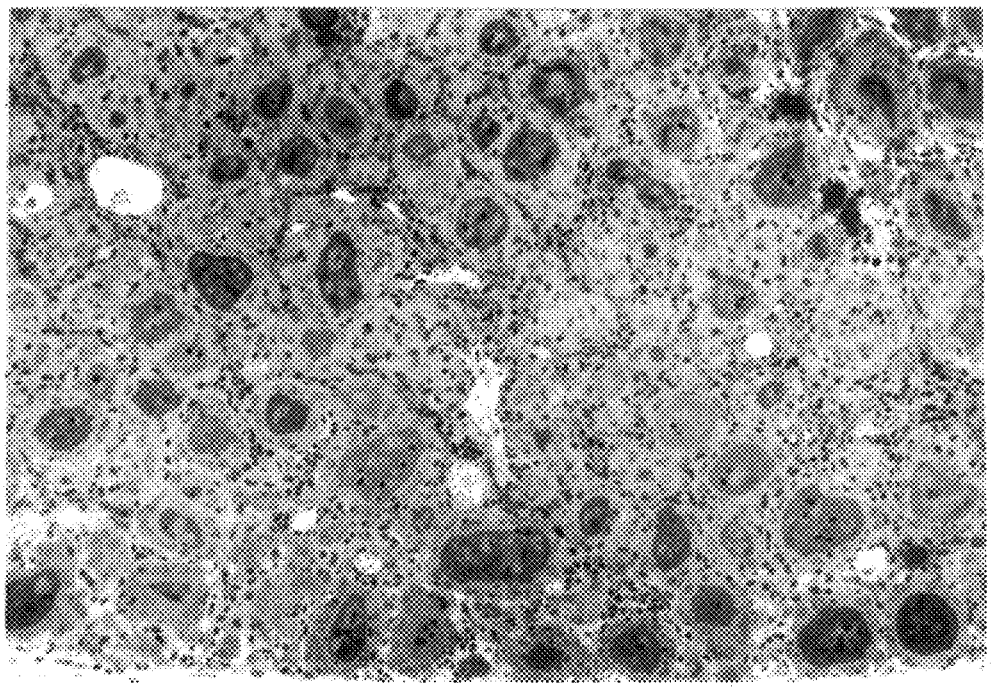
FIG. 1G shows parallel results when IL-4 was used.

The long term effect of the IL-9 therapy was studied by analyzing thyroid glands of the NOD mice, sixty four days after treatment on the high iodide diet described supra. The study of the thyroid glands paralleled those presented supra, and representative data are shown in FIGS. 1E and 1F, showing HID mice, and mice treated with IL-9, in addition to the HID diet. Figure 1E shows marked thyroiditis, while the biopsy shown in FIG. 1F demonstrates normal morphology, and evidences the fact that IL-9 did more than delay onset of autoimmune processes, and actually blocked them.

Further support for the conclusion that IL-9 had suppressed the cellular autoimmune response came from the data generated following the administration of IL-4, which is known as a major TH2 promoting factor. As will be seen in Table 1, and in FIG.1G, IL-4, when administered using the same protocol which was used for IL-9, did not inhibit iodide induced inflammation, while there was an increase in the levels of thyroid-infiltrating B cells, i.e., B220+ cells.

Figure 1H:
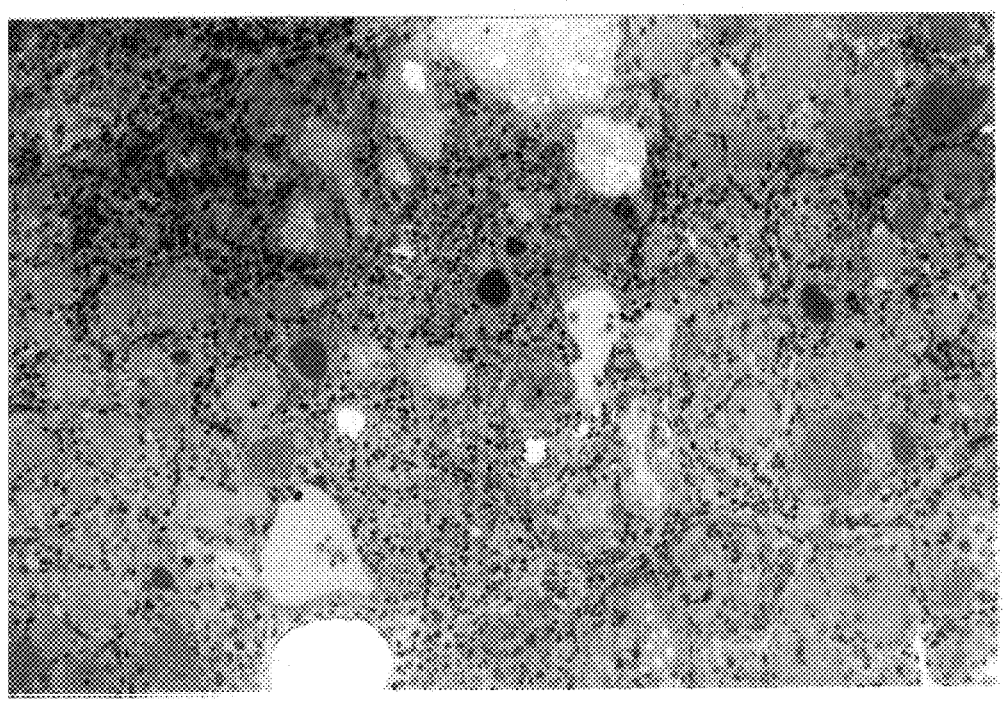
FIG. 1H shows induction of thyroiditis in animals previously rescued from thyroiditis by IL-9 administration.
Figure 2A:
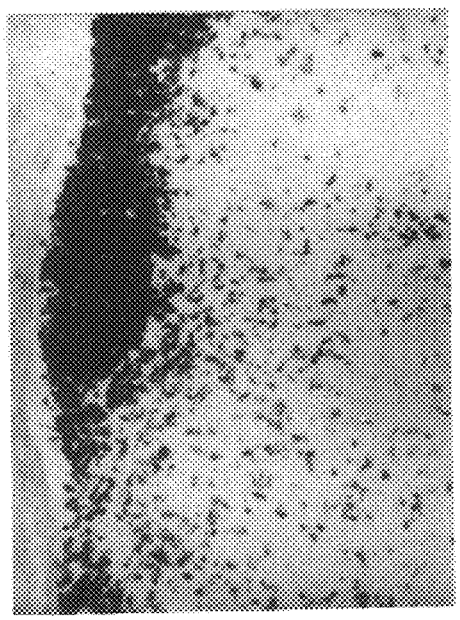
FIGS. 2A and 2B depict results of lymph node biopsies designed to measure B cell activation via immunostaining of B cells.
Figure 2B:
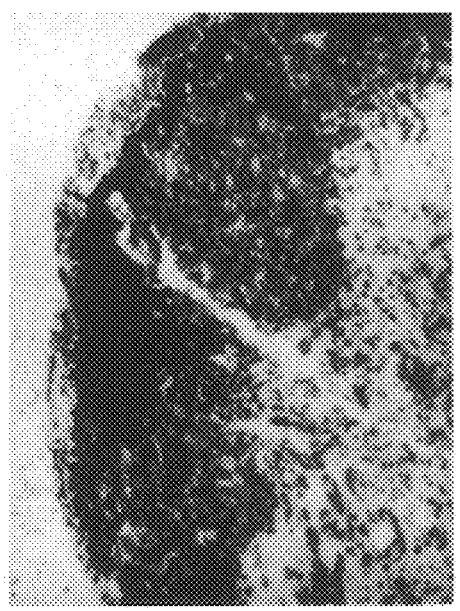

Yet further evidence came from a study in which mice, which had been protected via administration of IL-9 during a first HID regime were treated similarly, two months later. FIG. 1H shows that no resistance against iodide induced thyroiditis was detected, thus indicating that IL-9 does not support a protective memory response. Further analysis of the data does suggest that some B cell response is involved. For example, FIGS. 2A and 2B evidence B cell activation. Specifically, these figures show an analysis of draining lymph nodes of NOD mice, after HID treatment alone (examined at the fourth day of treatment), and with HID plus IL-9 (again, after four days). Germinal centers are enlarged in FIGS. 2A and 2B.

EXAMPLE 2

Figure 3:
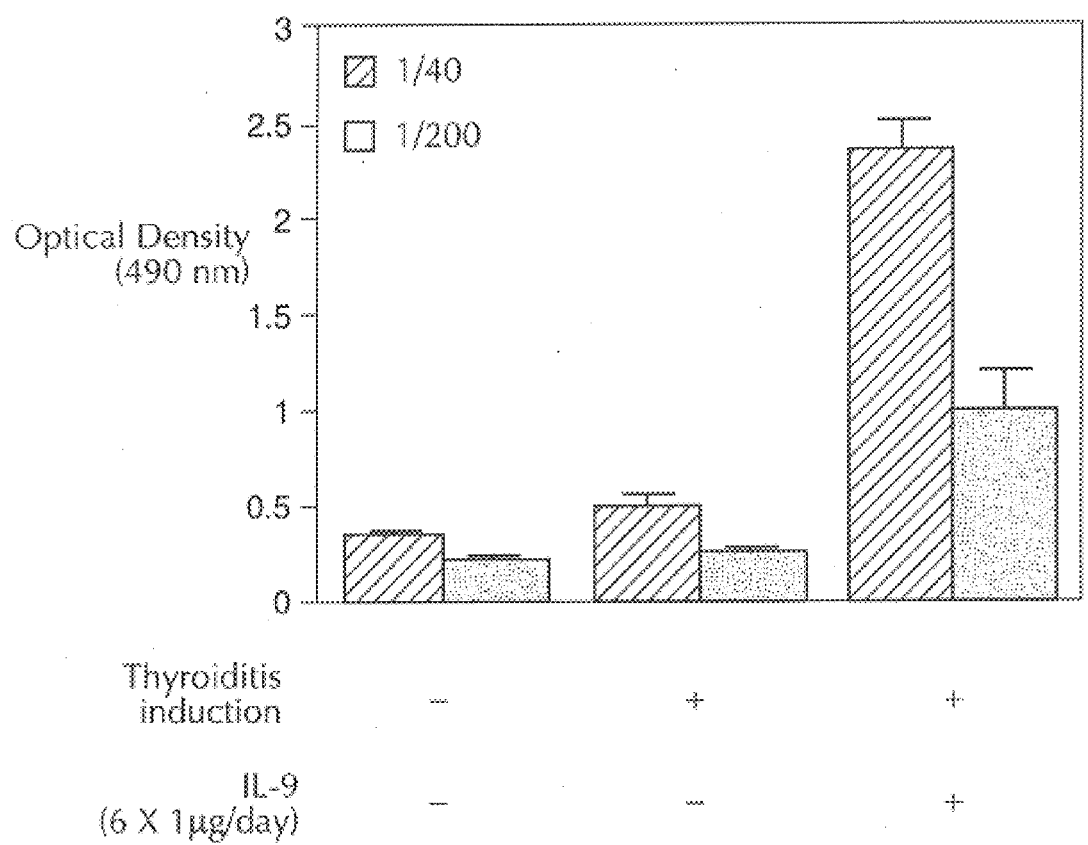
FIG. 3 shows results of ELISAs to determine anti-thyroglobulin antibodies in subject animals. Reading from left to right in this figure, it shows results taken from NOD mice without thyroiditis, NOD mice which received iodide only, and mice which received iodide and IL-9. The two optical densities come from two dilutions of tested serum.
Figure 4A:
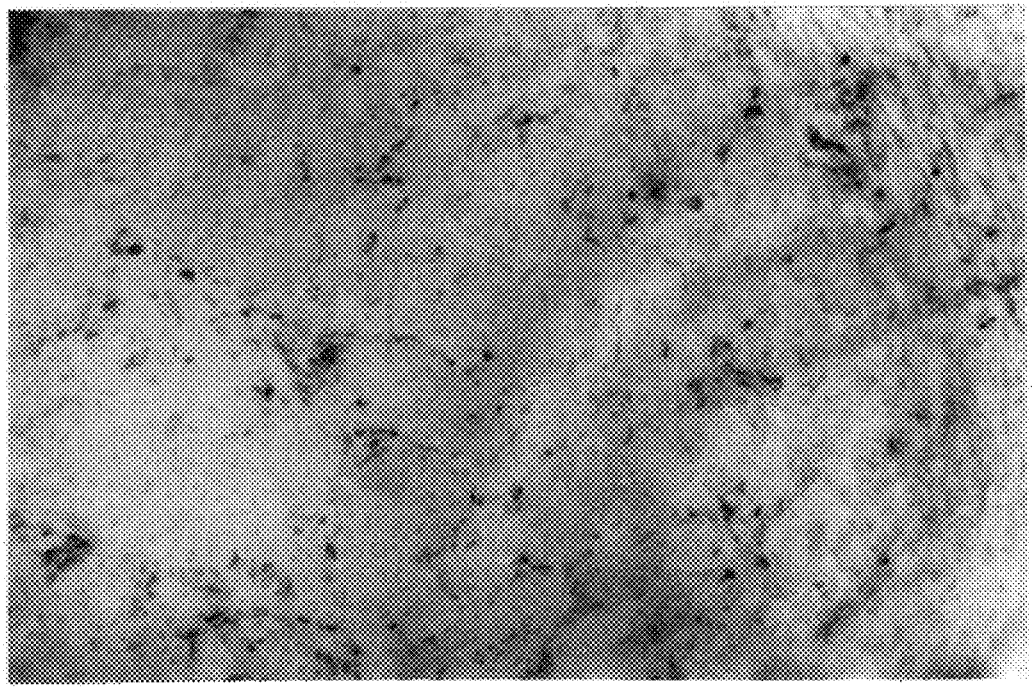
FIGS. 4A and 4B present immunostaining data for B cells in the thyroid of FVB mice.
Figure 4B:
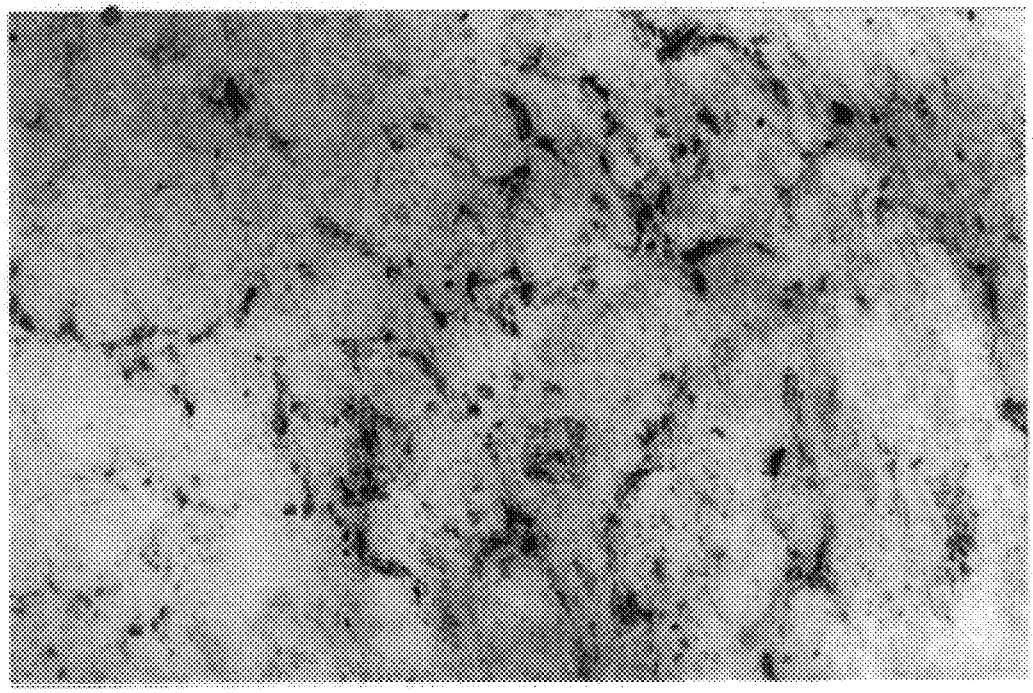

Further evidence of the phenomenon discussed above was found by carrying out a standard immunoassay (an ELISA) for anti-thyroglobulin antibodies. All measurements were taken at day four of either the HID diet alone, or HID and IL-9. As is shown in FIG. 3, the measurements were taken in a model where IL-9 was being administered once a day for six days. Two optical densities are shown for two different dilutions of the same serum, for NOD mice without thyroiditis for NOD mice which received iodide and no IL-9, and NOD mice where both iodide and IL-9 were administered. These run, left to right, in FIG. 3.

EXAMPLE 3

The observations reported supra, suggested extension to non-autoimmune disease prone mice. In these experiments, mice of FVB strain were treated with the high iodide diet, after they were fed a goitrogenic diet, just like the NOD mice.

It was found that, in this strain, IL-9 administration did not modify histological aspects of the thyroid gland, significantly increased the interstitium relative volume, provoked moderate increases in CD4+ cells, and a strong increase in B220+ infiltrating B220+ cells. This can be seen in Table II, supra, and FIGS. 4A and 4B.

In line with this, germinal center formation was increased in the draining lymph nodes of FVB mice, treated with IL-9, and the mice also showed anti-thyroglobulin antibodies, after four days.

These data indicate IL-9 stimulates B cell response in all animals tested.

An analysis of thyroxin content in plasma showed levels to be nearly the same. Non-IL-9 -injected mice had levels of 2.4±.08 ng/ml, while mice who had received injections of IL-9 showed levels of 2.2±0.6 ng/ml.

EXAMPLE 4

An additional study was carried out on a murine model for pancreas insulitis. Specifically, using the model, supra, the pancreas of 10 week old mice were examined following 6 days of administration of IL-9. See Table 3, which follows:

TABLE 3

|  | Iodide Only (5 mice) | Iodide & IL-9 (5 mice) |
| --- | --- | --- |
| Exp. 1 | 41.14 ± 8.05 | 10.9 ± 4.56 |
| Exp. 2 | 38.5 ± 2.4 | 11.5 ± 1.2 |

Figure 5:
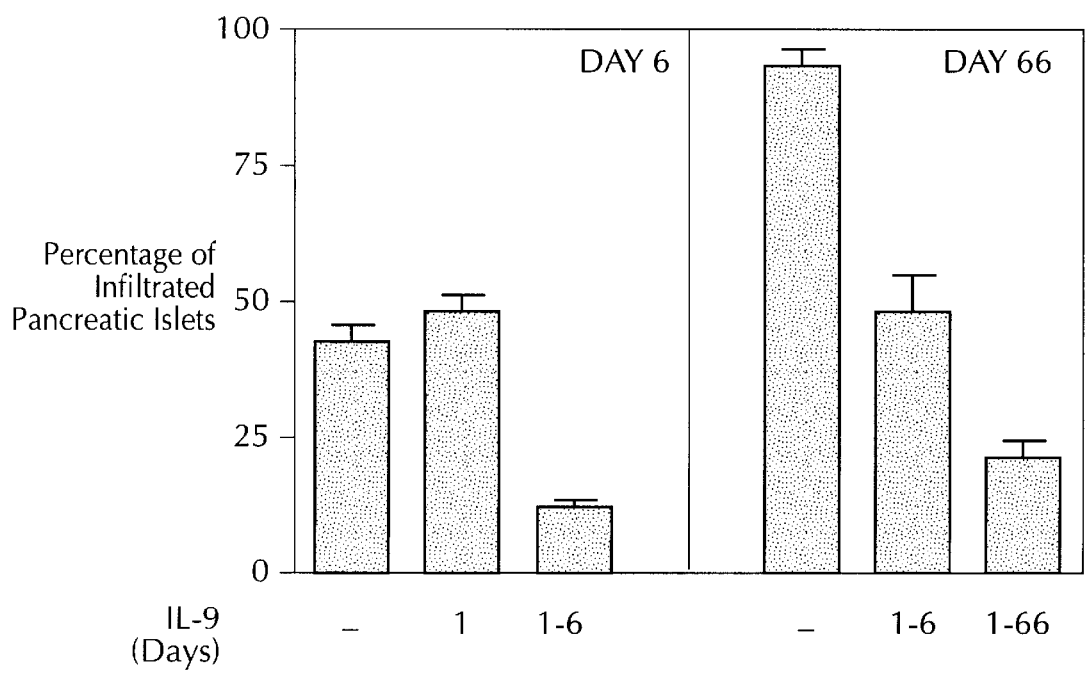
FIG. 5 presents results following a study of islets of Langerhans after administration of IL-9.
Figure 6A:
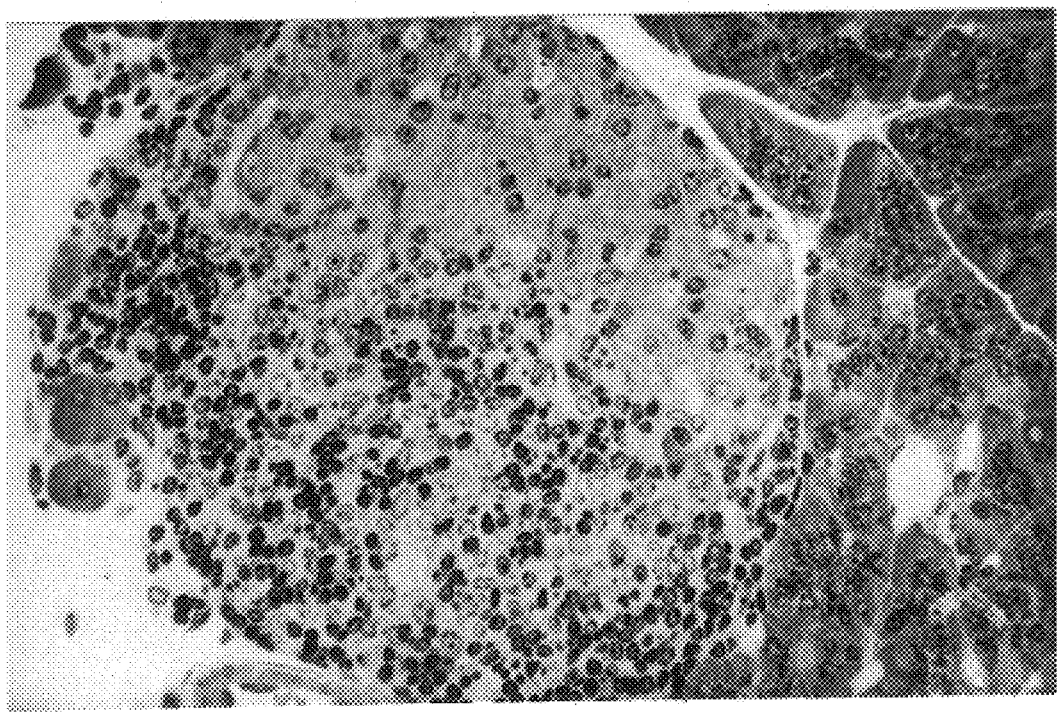
FIGS. 6A and 6B show the effect of IL-9 on pancreatic insulitis in NOD mice, where 6A shows islets of a 10 week old NOD mouse which received the high iodide diet and no IL-9, and 6B shows islets of a 10 week old, NOD mouse which received the HID diet and IL-9.
Figure 6B:
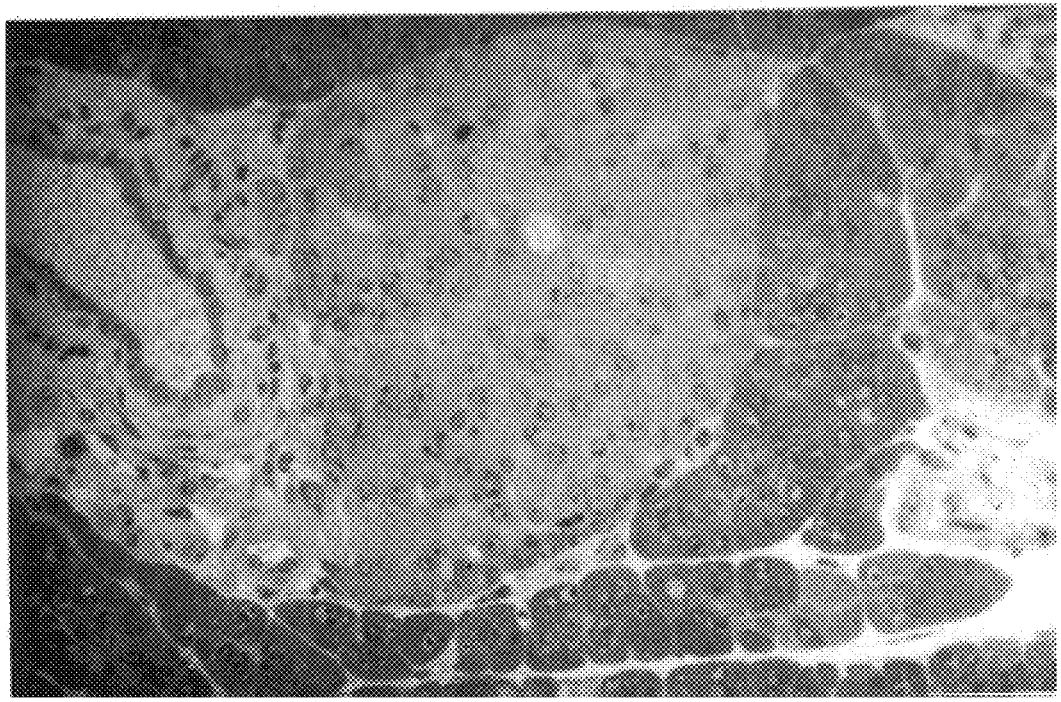

One group of NOD mice, i.e., the IL-9 group, received IL-9 (1 ug/injection), every three days, for 66 days, but no iodide treatment. The second group received either HID alone, or HID plus IL-9. These NOD mice were sacrificed at day 6, or day 66 of the experiment. This was two months after the end of treatment. As FIG. 5 shows, there was still a significantly lower percentage of inflamed islets. Finally, NOD mice received three weekly injections of IL-9, at from 10–18 weeks of age. In these mice, IL-9 mediated protection was increased, with only 20.9% of the islets showing inflammation, thus demonstrating a protective effect for the drug. Additional evidence of this is seen in FIGS. 6A and 6B, which compare pancreatic islets of untreated and treated NOD mice.

EXAMPLE 5

The FVB mouse used in the experiments, supra, is an appropriate model for study of interstitial lung diseases, such as silicosis. See, e.g., Kumar, Am. J. Pathol. 135: 605–614 (1989); Suzuki, et al., Thorax 51: 1036–1042 (1996), incorporated by reference.

Silica (DQ12, d50, 2.2 $\mu$m) or saline was injected directly into either normal FVB mice or a transgenic strain of FVB mice which overexpressed IL-9. Injection was via intratracheal instillation (100 ul/mouse). The animals had been anesthetized, using 2 mg of phenobarbital prior to treatment, and their necks had been surgically opened. Silica was sterilized, prior to use, by heating to 200° C. for four hours. This also inactivated endotoxin.

Figure 7A:
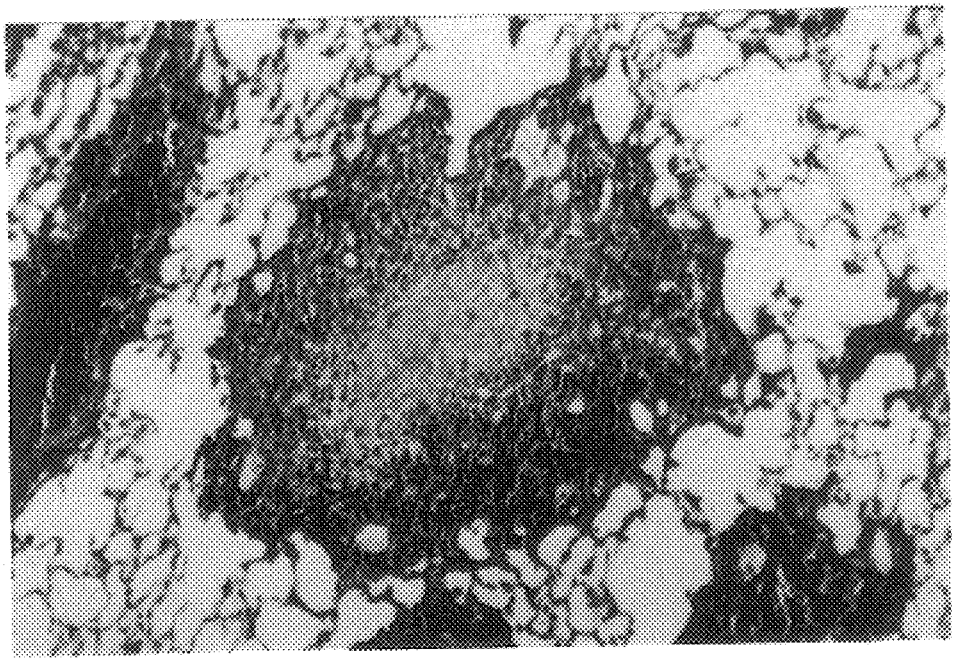
FIGS. 7A and 7B show histology of lungs of normal and IL-9 transgenic mice which received silica particles intratracheally.
Figure 7B:
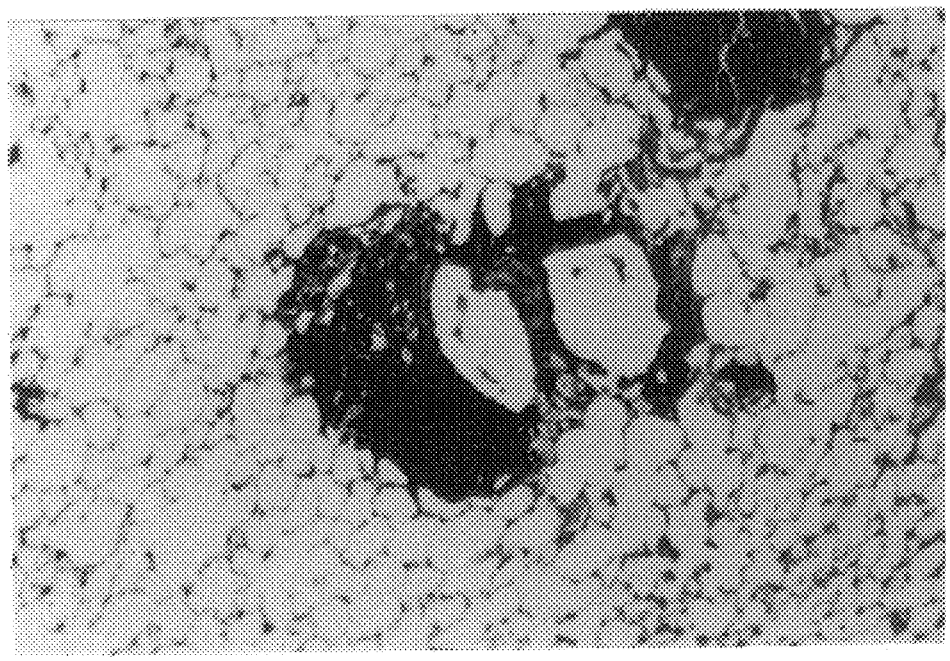

The mice received either 1 mg or 5 mg of silica in the 100 uls discussed supra. Mice were sacrificed either 60 days or 120 days after treatment and a bronchoalveolar lavage was performed via cannulating the trachea and infusing the lungs with 1.5 ml of 0.9% NaCl, six times. Collagen deposition was estimated by determining hydroxyproline content of the right lung. This was accomplished by excising the lung and homogenizing and hydrolyzing it in 6N HCl, overnight, at 110° C., followed by HPLC analysis. Left lungs were excised, and fixed in Bouin's solution for histopathology. Paraffin embedded sections were stained with hematoxylin and eosin, Masson's trichrome or toluidine blue for light microscopy. Histological examination showed multiple cellular nodules appeared rapidly after administration, which then converted to collagen containing nodules, with mesenchymal cells. See FIGS. 7A and 7B, which also shows that, in contrast, the TGIL-9 ("TGIL-9", which is an acronym for "transgenic IL-9 ") mice developed cellular nodules exclusively in the vicinity of blood vessels.

Figure 8:
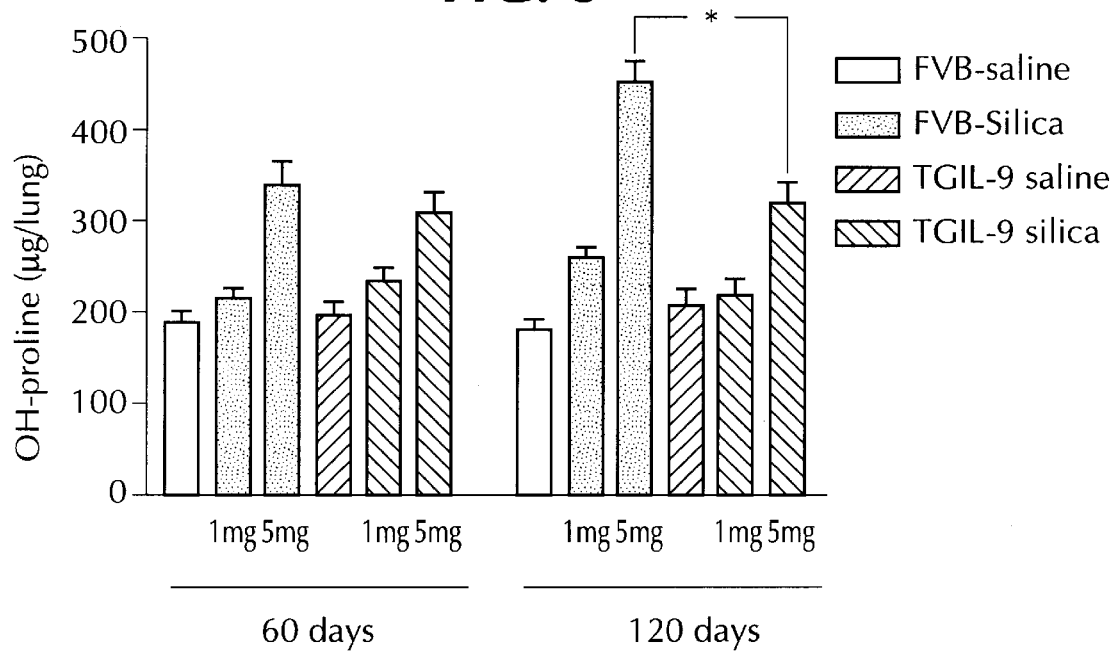
FIG. 8 shows hydroxyproline levels in the lungs of normal mice and transgenic mice which overproduce IL-9, which have been exposed to particles.

FIG. 8, which shows hydroxyproline levels, measured two months, and four months after administration confirm this. As will be seen from the figures, in those mice which over produce IL-9 the amount of hydroxyproline is significantly less at 120 days. Table 4 summarizes these results:

TABLE 4

|  | Normal Mice | TGIL-9 |
| --- | --- | --- |
| collagen accumulation | +++ | – |
| localization | alveolar walls | near vessels |
| cell types | mixed | B lymphocytes |

Figure 9:
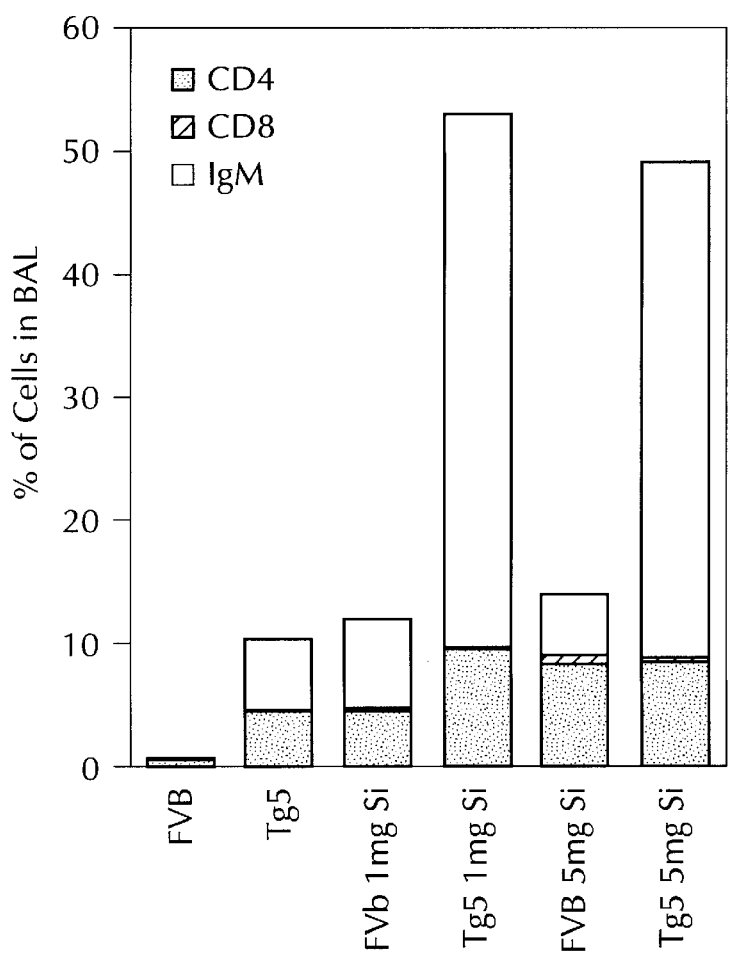
FIG. 9 shows FACS analysis of cells present in bronchoalveolar lavage of normal or IL-9 mice which were or were not treated with silica.

The broncho-alveolar lavage was assayed, and no significant differences were seen in the number of cells, when comparing silica treated normal and TGIL-9 mice; however, the TGIL-9 mice showed a significant increase in the percentage of lymphocytes, especially IgM+ B cells. See the analysis in FIG. 9. The lavage of normal mice, however, contained a majority of macrophages and neutrophils. There was no observed increase in immunoglobulin levels of the TGIL-9 mice. While the presence of B cells might be unrelated to anti-fibrotic effects of IL-9, it is consistent with the recognized fact that lymphocytes in broncho alveolar lavage of human patients is indicative of good prognosis. See Christman et al., Am. Rev. Respir. Dis. 132: 393–399 (1985).

The foregoing data show that, in appropriate animal models, IL-9 was effective in treating and preventing autoimmune pathologies associated with the thyroid gland, e.g., thyroiditis and with diabetes. Its antifibrotic effect is also shown, again in an appropriate animal model. As was pointed out, supra, the models used (the NOD and FVB mice), are useful in the study of other autoimmune pathologies, such as thyroiditis and autoimmune diabetes and fibrotic diseases such as silicosis. Hence, one aspect of the invention is a method for treating such disorders, via the administration of an effective amount of IL-9. The dosing regimen may vary, depending on the subject and the severity of the condition. In general, however, a dose of from about 500 ng to about 50 ug/kg of body weight of the subject, administered daily, is preferred; preferably, a dose of from about 1 ug to about 10 ug/kg of body weight is administered daily. The IL-9 may be naturally occurring, or recombinant in source, and may or may not be glycosylated. The cytokine can be administered via any standard therapeutic modality, such as via intravenous, intraperitoneal, sublingual, intradermal, subcutaneous, oral, intratracheal, intranasal or other forms of administration. The IL-9 may be administered alone, or in combination with pharmaceutically acceptable carriers, adjuvants, diluents, in aerosol form etc. Further, the IL-9 may be combined with one or more therapeutically effective material for treatment of the condition for which it is being used. Many drugs are used to treat diabetes, thyroiditis, and other cell mediated autoimmune disorders, such as IL-4. See, e.g., Rapoport, et al, J. Exp. Med. 178: 87–99 (1993). The IL-9 may be combined with these in pharmaceutical compositions and/or kits, wherein the therapeutically active IL-9 and the second drug may be combined (such as a composition), or in kit form, wherein separate portions of the drugs are made available for mixing at the convenience of the physician, patient, etc. Also a part of the invention is a method for blocking the inhibitory effect of IL-9 or its analogs on cellular immune responses, by administering an effective amount of an IL-9 antagonist, such as an antibody, soluble IL-9 receptor, a peptide based on IL-9 which inhibits interaction with receptors for IL-9, and so forth.

Other aspects of this invention will be clear to the skilled artisan and need not be discussed further.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for treating or preventing interstitial lung disease, comprising administering to a subject in need thereof an amount of IL-9 sufficient to prevent or treat interstitial lung in said subject.

2. The method of claim 1, wherein said interleukin-9 is human interleukin 9.

3. The method of claim 1, wherein said interleukin-9 is produced recombinantly.

4. The method of claim 1, wherein said interleukin-9 is administered intravenously, intraperitoneally, transdermally, subcutaneously, orally, intratracheally or sublingually.

5. The method of claim 1, comprising administering said interleukin 9 in an amount from about 500 ng to about 50 ug/kg of body weight.

6. The method of claim 1, wherein said interstitial lung disease is silicosis.

* * * * *